US010271769B2

(12) United States Patent
Miyasaka et al.

(10) Patent No.: US 10,271,769 B2
(45) Date of Patent: Apr. 30, 2019

(54) PERFORMANCE INFORMATION NOTIFICATION DEVICE AND PERFORMANCE INFORMATION NOTIFICATION METHOD

(71) Applicant: SEIKO EPSON CORPORATION, Tokyo (JP)

(72) Inventors: Eiji Miyasaka, Okaya (JP); Osamu Yamada, Chino (JP)

(73) Assignee: SEIKO EPSON CORPORATION, Tokyo (JP)

( * ) Notice: Subject to any disclaimer, the term of this patent is extended or adjusted under 35 U.S.C. 154(b) by 0 days.

(21) Appl. No.: 15/462,049

(22) Filed: Mar. 17, 2017

(65) Prior Publication Data
US 2017/0274247 A1    Sep. 28, 2017

(30) Foreign Application Priority Data

Mar. 28, 2016 (JP) ................ 2016-063265

(51) Int. Cl.
*A63B 24/00* (2006.01)
*A63B 71/06* (2006.01)
(Continued)

(52) U.S. Cl.
CPC ............ *A61B 5/11* (2013.01); *A61B 5/1118* (2013.01); *G06K 9/00342* (2013.01); *G06K 9/00523* (2013.01); *G07C 1/22* (2013.01); *G07C 1/28* (2013.01); *G16H 20/30* (2018.01); *G16H 40/63* (2018.01); *G16H 50/30* (2018.01); *A61B 5/02438* (2013.01); *A61B 5/681* (2013.01); *A61B 5/742* (2013.01); *A61B 2503/10* (2013.01); *A63B 2230/00* (2013.01)

(58) Field of Classification Search
CPC ............ A63B 24/0062; A63B 24/0075; A63B 24/0006; A63B 2230/00; A61B 5/11; A61B 5/1118; A61B 5/02438; A61B 5/742; A61B 5/681; A61B 2503/10; G16H 50/30; G16H 40/63; G16H 20/30; G06K 9/00342; G06K 9/00523; G07C 1/22; G07C 1/28
See application file for complete search history.

(56) References Cited

U.S. PATENT DOCUMENTS 4,566,461 A * 1/1986 Lubell .................... A61B 5/024
377/24.2
5,879,270 A * 3/1999 Huish .................... A63B 22/02
482/1
(Continued)

FOREIGN PATENT DOCUMENTS

JP      2000-288148 A    10/2000
JP      2012-020134 A     2/2012
(Continued)

*Primary Examiner* — Adnan Aziz
(74) *Attorney, Agent, or Firm* — Oliff PLC

(57) ABSTRACT

A performance information notification device according to an application example includes: an acquisition unit which acquires information indicating at least one of load exercise and rest in interval exercise; and a notification unit which reports performance information about at least one of a time during which the load exercise is carried out and a time during which the rest is carried out, based on the information indicating at least one of the load exercise and the rest.

17 Claims, 13 Drawing Sheets

(51) Int. Cl.
*A61B 5/11* (2006.01)
*G06K 9/00* (2006.01)
*G07C 1/22* (2006.01)
*G07C 1/28* (2006.01)
*G16H 40/63* (2018.01)
*G16H 50/30* (2018.01)
*G16H 20/30* (2018.01)
*A61B 5/00* (2006.01)
*A61B 5/024* (2006.01)

(56) References Cited

U.S. PATENT DOCUMENTS

| | | | |
|---|---|---|---|
| 7,534,206 B1 * | 5/2009 | Lovitt | A61B 5/02438 |
| | | | 482/8 |
| 7,717,827 B2 * | 5/2010 | Kurunmaki | A63B 24/0062 |
| | | | 434/247 |
| 9,084,912 B2 * | 7/2015 | Jaquish | A63B 21/00047 |
| 2006/0004265 A1 * | 1/2006 | Pulkkinen | A61B 5/0205 |
| | | | 600/300 |
| 2006/0183603 A1 * | 8/2006 | Astilean | A63B 22/0242 |
| | | | 482/8 |
| 2008/0096726 A1 * | 4/2008 | Riley | A63B 24/0006 |
| | | | 482/8 |
| 2008/0200312 A1 * | 8/2008 | Tagliabue | G01C 22/006 |
| | | | 482/9 |
| 2009/0048070 A1 * | 2/2009 | Vincent | A63B 24/0021 |
| | | | 482/8 |
| 2010/0317489 A1 * | 12/2010 | Flaction | A61B 5/11 |
| | | | 482/9 |
| 2011/0035184 A1 * | 2/2011 | Aaron | A63B 24/0006 |
| | | | 702/158 |
| 2012/0015778 A1 | 1/2012 | Lee et al. | |
| 2012/0075959 A1 * | 3/2012 | Keith | G04F 3/08 |
| | | | 368/11 |
| 2013/0123071 A1 * | 5/2013 | Rhea | A63B 24/00 |
| | | | 482/8 |
| 2014/0073486 A1 * | 3/2014 | Ahmed | A61B 5/02405 |
| | | | 482/9 |
| 2015/0099991 A1 | 4/2015 | Yamaguchi et al. | |
| 2015/0258384 A1 * | 9/2015 | Suzuki | A63B 24/0087 |
| | | | 482/5 |
| 2015/0309480 A1 * | 10/2015 | Patton | G04F 1/005 |
| | | | 368/109 |
| 2015/0324751 A1 * | 11/2015 | Orenstein | G06F 19/3481 |
| | | | 702/3 |
| 2016/0081620 A1 * | 3/2016 | Narayanan | A61B 5/4866 |
| | | | 600/483 |
| 2016/0121162 A1 * | 5/2016 | Deutsch | G06F 16/60 |
| | | | 482/4 |
| 2016/0151673 A1 | 6/2016 | Shinayama et al. | |
| 2016/0342311 A1 * | 11/2016 | Homick | H04W 4/80 |
| 2017/0143262 A1 * | 5/2017 | Kurunmaki | A61B 5/0255 |

FOREIGN PATENT DOCUMENTS

JP 2015-073590 A 4/2015
WO 2015-015564 A1 2/2015

* cited by examiner

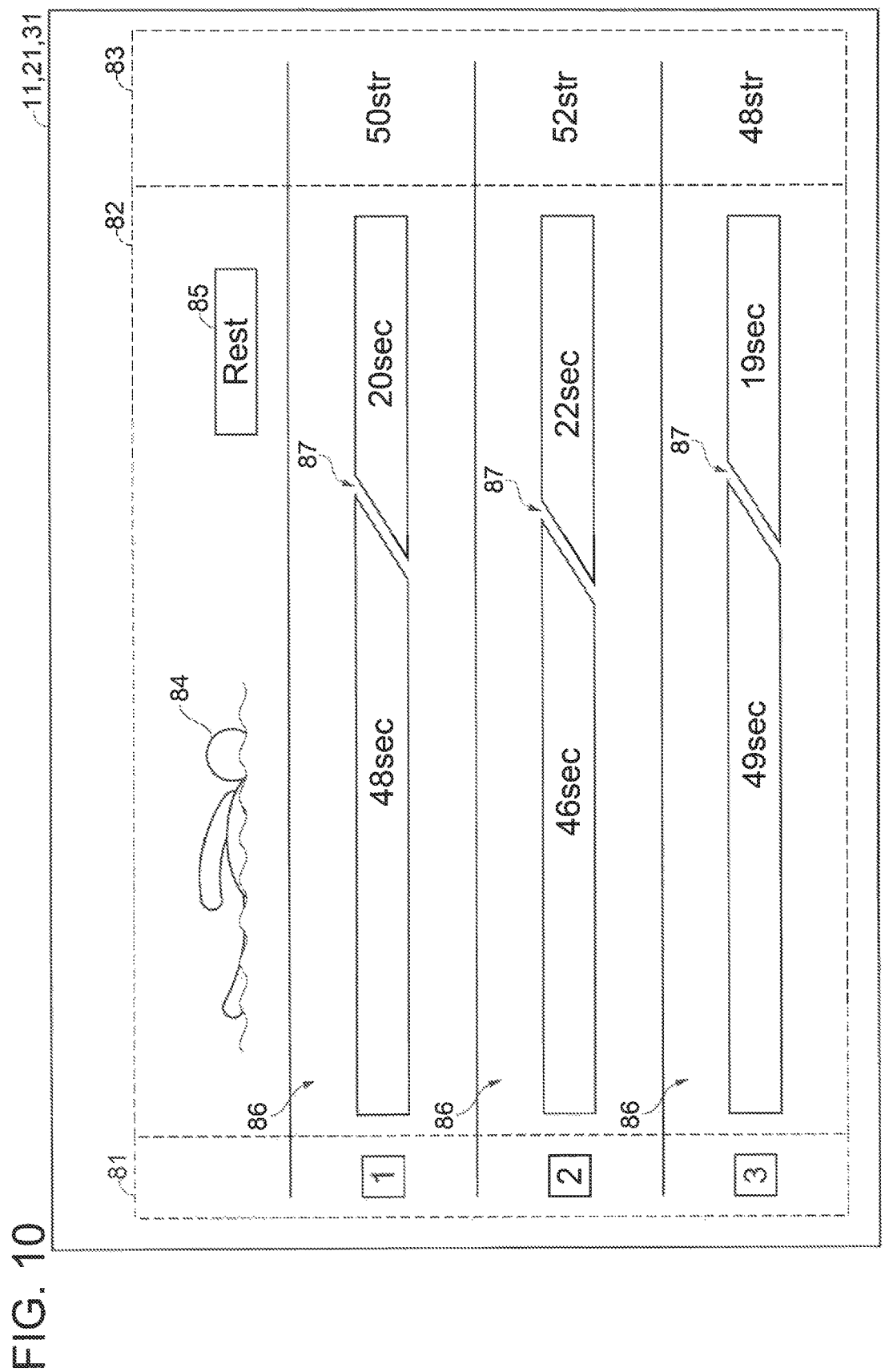

PERFORMANCE INFORMATION NOTIFICATION DEVICE AND PERFORMANCE INFORMATION NOTIFICATION METHOD

BACKGROUND

1. Technical Field

The present invention relates to a performance information notification device and a performance information notification method.

2. Related Art

Generally, sports players wish to improve their own records and performance in the sports they are involved in, and to this end, they make efforts to enhance their cardiopulmonary function and improve their physical abilities, introducing various training methods. As a training method to this end, interval exercise (also called interval training) is considered very effective. Interval exercise is a training method in which high-load exercise and low-load exercise or rest are alternately repeated a predetermined number of times. With interval exercise, not only sports players but also ordinary people who enjoy sports as a hobby can improve their physical abilities by carrying out interval exercise workouts suitable for their own levels. Hereinafter, in this specification, sports players and ordinary people who enjoy sports are collectively called athletes.

In a common interval exercise workout, the athlete manages exercise intensity by deciding the durations of high-load exercise and low-load exercise, or the exercise distance and the number of times of repetition or the like. For this purpose, an electronic device which calculates one or both of the duration of high-load exercise and the duration of low-load exercise in interval exercise is proposed (see WO2015/015564, for example).

Incidentally, in swimming or the like, one exercise cycle is made up of one session of high-load exercise and one session of low-load exercise or rest. The duration of one exercise cycle (one period) is decided and interval exercise is carried out by repeating multiple exercise cycles. In this training method, for example, the athlete swims a predetermined distance within one predetermined period (that is, carries out high-load exercise) and then rests until the next one period begins.

In the case where the athlete decides one period of exercise cycle and the number of times and thus carries out interval exercise, it is important for the athlete to know information about training such as the timing when the one period of exercise cycle begins, to what degree the high-load exercise and the low-load exercise are carried out within the one period, or the number of exercise cycles.

However, with respect to interval exercise by such a method, there are not enough devices proposed which enable easy confirmation of information about training or which facilitate management of the duration of training, the result of training and like.

SUMMARY

An advantage of some aspects of the invention is to provide a performance information notification device and a performance information notification method suitable for interval exercise in which one period of exercise cycle and the number of times are decided.

The invention can be implemented as the following configurations or application examples.

Application Example 1

A performance information notification device according this application example includes: an acquisition unit which acquires information indicating at least one of load exercise and rest in interval exercise; and a notification unit which reports performance information about at least one of a time during which the load exercise is carried out and a time during which the rest is carried out, based on the information indicating at least one of the load exercise and the rest.

According to this application example, the performance information notification device acquires information indicating at least one of load exercise and rest in interval exercise and reports performance information about the time during which the load exercise is carried out or the time during which the rest is carried out, in the interval exercise.

Therefore, with the notification from the performance information notification device, the athlete can learn about the time during which the load exercise is carried out or the time during which the rest is carried out, in the interval exercise.

Application Example 2

In the application example, it is desirable that the performance information includes at least one of a cumulative value of the time during which the load exercise is carried out in the interval exercise and a cumulative value of the time during which the rest is carried out in the interval exercise.

According to this application example, the athlete can be notified of the cumulative value of the time during which the load exercise is carried out in the interval exercise or the cumulative value of the time during which the rest is carried out in the interval exercise, as the performance information.

Application Example 3

In the application example, it is desirable that the performance information includes at least one of a proportion of a cumulative value of the time during which the load exercise is carried out to a time during which the interval exercise is carried out, and a proportion of a cumulative value of the time during which the rest is carried out to the time during which the interval exercise is carried out.

According to this application example, the athlete can be notified of proportion of the cumulative time of exercise or the cumulative time of rest to the time during which one session of interval exercise is carried out, as the performance information.

Application Example 4

In the application example, it is desirable that the interval exercise includes at least one exercise cycle made up of one session of the load exercise and one session of the rest, and that the performance information includes at least one of a time during which the load exercise is carried out in the one exercise cycle and a time during which the rest is carried out in the one exercise cycle.

According to this application example, the athlete can be notified of the time during which the load exercise is carried out or the time during which the rest is carried out, in one exercise cycle during the interval exercise, as the performance information.

Application Example 5

In the application example, it is desirable that the interval exercise includes at least one exercise cycle made up of one session of the load exercise and one session of the rest, and that the performance information includes at least one of a proportion of a time during which the load exercise is carried out to a time during which the one exercise cycle is carried out, and a proportion of a time during which the rest is carried out to the time during which the one exercise cycle is carried out.

According to this application example, the athlete can be notified of the proportion of the time during which the load exercise is carried out or the time during which the rest is carried out, to the time during which one exercise cycle is carried out, as the performance information.

Application Example 6

In the application example, it is desirable that the acquisition unit includes a sensor which detects a movement of a person.

According to this application example, the acquisition unit of the performance information notification device includes a sensor which detects a movement of a person. Therefore, for example, in the case where the performance information notification device is mounted on an athlete, the information indicating at least one of the load exercise and the rest of the athlete can be acquired by the acquisition unit.

Application Example 7

In the application example, it is desirable that the device further includes a clocking unit which measures a time elapsed, and that the notification unit reports the performance information generated, based on the time elapsed and the information indicating at least one of the load exercise and the rest.

According to this application example, the performance information notification device can report the performance information generated, based on the time elapsed and the information indicating the load exercise or the rest.

Application Example 8

In the application example, it is desirable that the acquisition unit includes a communication unit which sends and receives information, and acquires the information indicating at least one of the load exercise and the rest, via the communication unit.

According to this application example, the acquisition unit includes a communication unit which sends and receives information. Therefore, the performance information notification device can acquire the information indicating at least one of the load exercise and the rest, via the communication unit.

Application Example 9

A performance information notification method according to this application example includes: acquiring information indicating at least one of load exercise and rest in interval exercise; and reporting performance information about at least one of a time during which the load exercise is carried out and a time during which the rest is carried out, based on the information indicating at least one of the load exercise and the rest.

According to this application example, information during the time when the athlete is carrying out training by interval exercise is acquired. Therefore, with the notification from the performance information notification device, the athlete can learn the performance information about training.

Application Example 10

A performance information notification program according to this application example is a computer-readable program causing a computer to execute: acquiring information indicating at least one of load exercise and rest in interval exercise; and reporting performance information about at least one of a time during which the load exercise is carried out and a time during which the rest is carried out, based on the information indicating at least one of the load exercise and the rest.

According to this application example, information during the time when the athlete is carrying out training by interval exercise is acquired. Therefore, with the notification from the performance information notification device, the athlete can learn the performance information about training.

BRIEF DESCRIPTION OF THE DRAWINGS

The invention will be described with reference to the accompanying drawings, wherein like numbers reference like elements.

FIG. 10 shows another example of display on the performance information notification device.

DESCRIPTION OF EXEMPLARY EMBODIMENTS

Embodiment

Figure 1:
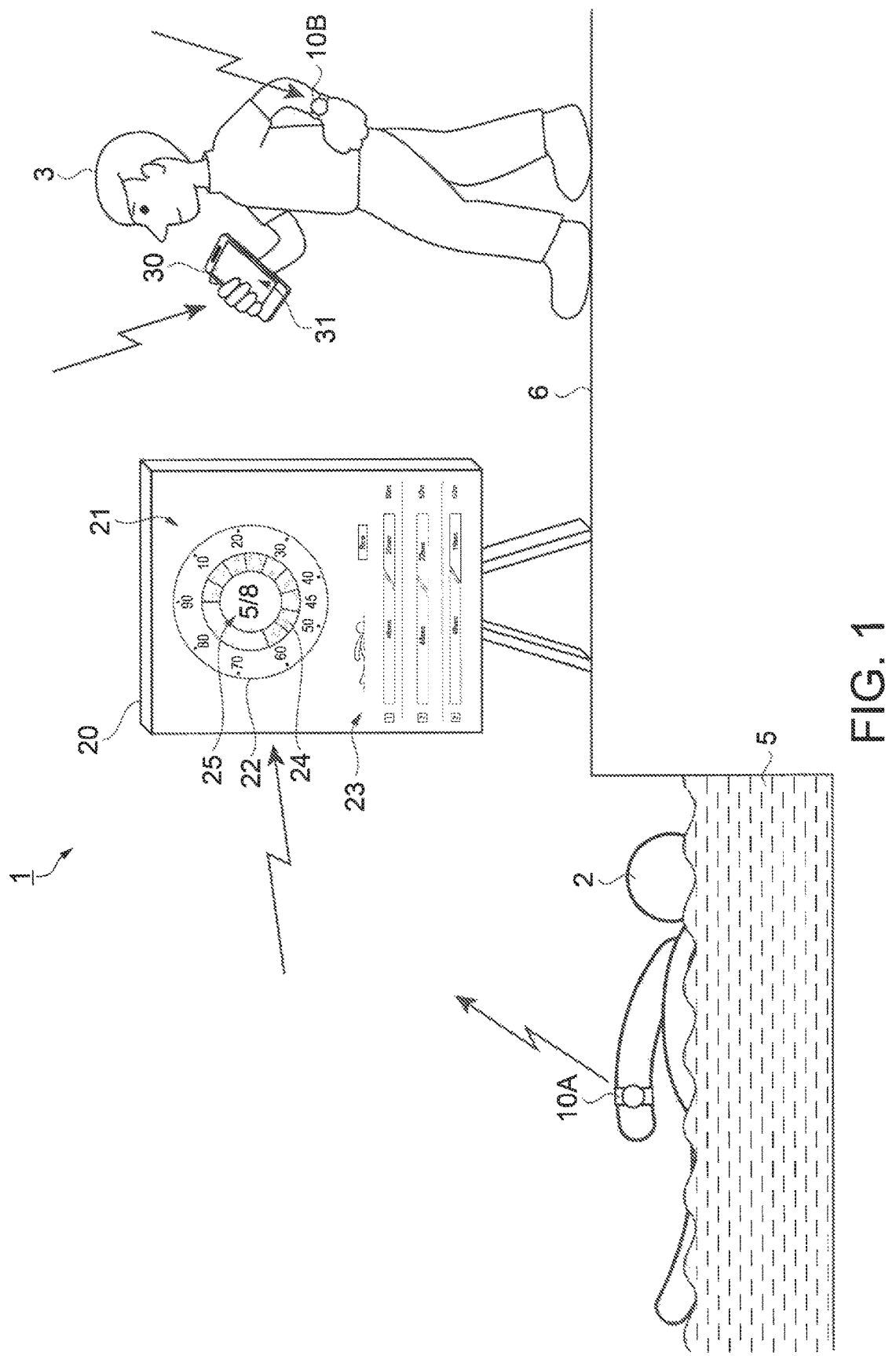
FIG. 1 is a conceptual view showing a mode of use of a performance information notification system according to an embodiment of the invention.

Hereinafter, an embodiment of a performance information notification device according to the invention will be described with reference to the drawings. In the embodiment, a performance information notification device used in the case of carrying out interval exercise in swimming training is employed as an example.

In the drawings referred to in the description below, some members or parts may not be shown to scale vertically or horizontally, for the sake of convenience of the description and illustrations. Also, elements which are not necessary for the explanation may be omitted.

Overall Configuration of Performance Information Notification System

FIG. 1 is a conceptual view showing a mode of use of a performance information notification system 1 according to an embodiment of the invention. As shown in FIG. 1, the performance information notification system 1 includes an information device 10 (10A or 10B), an electronic display board 20, and a portable information terminal 30, for example. Alternatively, the information device 10 (10A or 10B) can independently serve as the performance information notification system 1. The information device 10 (10A or 10B), the electronic display board 20, and the portable information terminal 30 are an example of a performance information notification device in the performance information notification system 1.

The information device 10 (10A or 10B) is an electronic device which acquires information indicating at least one of load exercise and rest in interval exercise (hereinafter referred to as exercise/rest information).

The information device 10 (10A or 10B) further includes an information notification function in the performance information notification system 1. That is, the information device 10 (10A or 10B) can generate information about at least one of the time during which the load exercise is carried out and the time during which the rest is carried out (hereinafter referred to as performance information), based on the exercise/rest information, and can notify the outside of the performance information via a display, notification sound, or vibration or the like. Therefore, the information device 10 (10A or 10B) can function as a performance information notification device which acquires the exercise/rest information and notifies the outside of the performance information.

Moreover, the information device 10 (10A or 10B) can communicate with an external device and can notify the external device of the acquired exercise/rest information and the generated performance information or the like. In the mode of use shown in FIG. 1, the information device 10A notifies the information device 10B, the electronic display board 20, or the portable information terminal 30, as an external device, of the exercise/rest information and the performance information or the like. The external device notifies the outside of the performance information via a display, notification sound, or vibration or the like, based on the received information.

In the embodiment, the information device 10 (10A or 10B) is a wrist-worn electronic device which is wound around the wrist.

In the mode of use shown in FIG. 1, the information device 10A is worn around a wrist of an athlete 2 carrying out interval exercise in a swimming pool 5. Therefore, the information device 10A can acquire exercise/rest information of the athlete 2 and inform (notify) the athlete 2 of performance information generated based on the exercise/rest information. That is, the information device 10A functions as a performance information notification device.

Meanwhile, the information device 10B is used, worn around a wrist of a coach 3 on a poolside 6. The information device 10B notifies the coach 3 of the performance information of the athlete 2 received from the information device 10A, in the same form as the information device 10A. The information device 10B, acquiring the performance information of the athlete 2 and notifying the coach 3 of the performance information, is another example of the performance information notification device. Therefore, the coach 3 can guide the athlete 2 while viewing the same display as the display viewed by the athlete 2. Moreover, though not shown in FIG. 1, the information device 10B can communicate with an external device as described above and therefore can send information to the information device 10A. Thus, for example, by having the coach 3 send an instruction on training from the information device 10B to the information device 10A, the athlete 2 can check the instruction and then do his/her training.

The electronic display board 20 is an electronic device mainly achieving the information notification function in the performance information notification system 1. The electronic display board 20 has a display screen 21 which is larger than a display screen 11 (see FIG. 2) provided in the information device 10 (10A or 10B), and displays performance information based on information received from the information device 10A, thus giving a notification to the outside. The electronic display board 20, acquiring the performance information of the athlete 2, displaying the performance information on the display screen 21 and thus giving a notification to the outside, is another example of the performance information notification device. As the electronic display board 20 is installed on the poolside 6, not only the athlete 2 during interval exercise and the coach 3, but also other athletes training with the athlete 2 and spectators can check the performance information of the athlete 2.

As will be described in detail later, performance information is displayed in various forms on the display screen 21 of the electronic display board 20. In the embodiment of FIG. 1, the time during which load exercise is carried out for each period is displayed as performance information. On the display screen 21, a pie chart 22 and a bar chart 23 are displayed. The pie chart 22 shows the lapse of time as display segments 24 are gradually lit. In the pie chart 22, the time (period) of one exercise cycle in interval exercise is expressed by the time until all of the display segments 24 are lit (in FIG. 1, 90 seconds), and the time elapsed during which load exercise is carried out (in FIG. 1, 60 seconds) is indicated by the lighting position of the display segments 24.

In a center part 25 of the pie chart 22, information about the number of exercise cycles is displayed. FIG. 1 shows that five of eight exercise cycles are finished. In the bar chart 23, three bars are displayed. Each bar shows information about the time during which load exercise is carried out and the time during which rest is carried out (performance information) for each exercise cycle.

The portable information terminal 30 is a portable electronic device such as a smartphone or tablet. Generally, the portable information terminal 30 has a display screen 31 that is larger than the display screen of the wrist-worn information device 10 (10A or 10B), and a higher information processing capacity. Therefore, with the portable information terminal 30, the exercise/rest information or the performance information or the like received from the wrist-worn information device 10A can be easily checked. Also, the portable information terminal 30 can process, manage or report the exercise/rest information or the performance information or the like with various kinds of application software provided therein. The portable information terminal 30, acquiring the performance information of the athlete 2 and processing, managing or reporting the performance information with various kinds of application software provided therein, is another example of the performance information notification device. As a result, for example, the coach 3 can compare the current performance information of the athlete 2 with the past performance information of the athlete 2 or with the performance information of other athletes and then notify the athlete 2, using the portable information terminal 30.

Information Device

Next, the information device 10 (10A or 10B) will be described further in detail.

Figure 2:
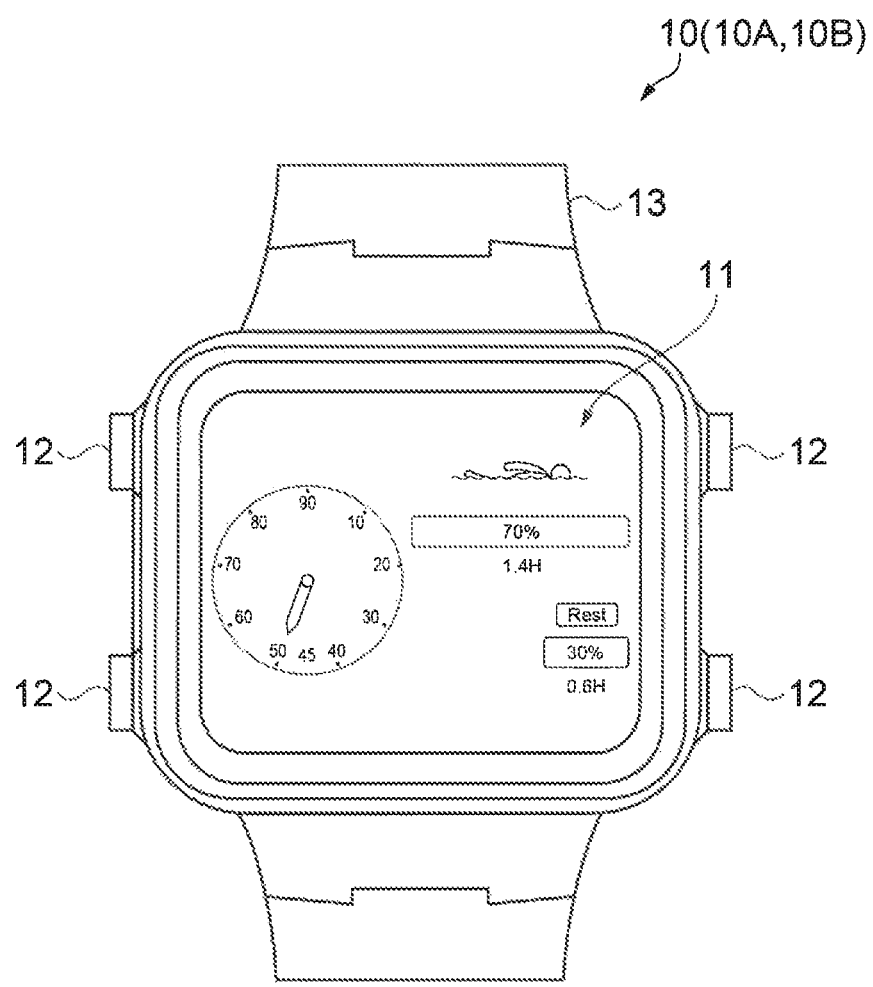
FIG. 2 is an external view showing an example of a performance information notification device in the performance information notification system.

FIG. 2 is an external view showing an example of the information device 10 (10A or 10B) as the performance information notification device in the performance information notification system 1. Here, a wrist-worn electronic device is employed as an example. The information device 10 (10A or 10B) has a display screen 11, buttons 12, and a band 13.

As will be described in detail later, performance information is displayed in various formed on the display screen 11. In the embodiment of FIG. 2, a circular analog display-type timer with a pointer and a bar chart are displayed.

The circular analog display-type timer shows the time during which load exercise is carried out in one period of exercise cycle, as performance information. In the circular analog display-type timer, one period of exercise cycle in interval exercise is displayed as the time for the pointer to make a round (in FIG. 2, 90 seconds), and the time elapsed (in FIG. 2, 50 seconds) is indicated by the current position of the pointer. One period can be set via the buttons 12 or the like of an operation unit 160 (see FIG. 3), and the set one period is evenly distributed within the circle of the circular analog display-type timer. Therefore, as the pointer makes a round, the display shows that the set one period passes. Thus, the athlete 2 can learn the time during which load exercise is carried out and the rest time until the next exercise cycle begins, by checking the position of the pointer when finishing the load exercise. Also, the athlete 2 can learn at a glance that the pointer reaches a predetermined position (in FIG. 2, the display position of 90). Therefore, the athlete 2 can easily pay attention not to delay the start of the next exercise cycle.

The bar chart shows the cumulative value of the time during which load exercise is carried out (cumulative time of exercise) and the cumulative value of the time during which rest is carried out (cumulative time of rest) in one session of interval exercise, in the form of the length of the bar chart, as one piece of performance information. The cumulative time of exercise and the cumulative time of rest are displayed in the form of numerical values near the bar chart. Also, the proportion of the cumulative time of exercise to the time during which one session of interval exercise is carried out (first proportion of exercise) and the proportion of the cumulative time of rest to the time during which one session of interval exercise is carried out (first proportion of rest) are displayed by the percentage on the bar chart as another piece of performance information. In the display example of FIG. 2, the cumulative time of exercise 1.4 H is shown near the bar chart, and the first proportion of exercise 70% is shown on the bar chart. The cumulative time of rest 0.6 H is shown near the bar chart, and the first proportion of rest 30% is shown on the bar chart.

The buttons 12 are input members used by the athlete 2 and the coach 3 or the like (hereinafter referred to as the user) when operating the information device 10 (10A or 10B). The band 13 is used by the user to wear the information device 10 (10A or 10B) on the wrist.

Configuration of Performance Information Notification System

Next, the configuration of the performance information notification system 1 and the functional configuration of the performance information notification device will be described.

Figure 3:
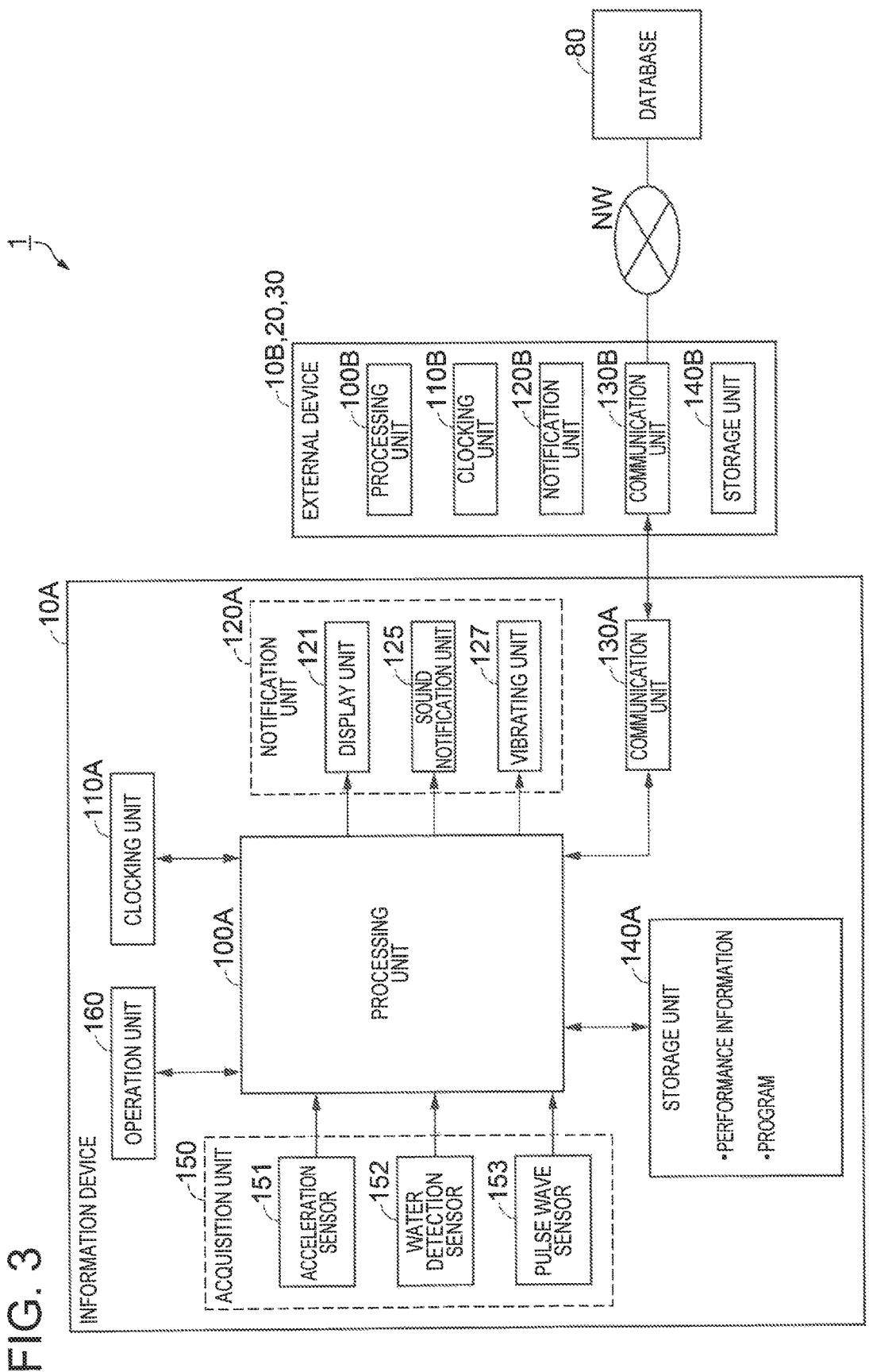
FIG. 3 shows the configuration of the performance information notification system.

FIG. 3 shows the configuration of the performance information notification system 1. FIG. 3 also shows the functional configurations of the information device 10A and the external device 10B, 20, 30 (information device 10B, electronic display board 20, or portable information terminal 30), as performance information notification devices.

As described above, the performance information notification system 1 includes the information device 10 (10A or 10B) and the electronic display board 20 or the portable information terminal 30. The performance information notification system 1 may also include a database 80 connected via a network NW, as shown in FIG. 3.

Functional Configuration of Information Device

The information device 10A worn by the athlete 2 and the information device 10B carried by the coach 3 as the external device 10B, 20, 30 have the same functional configuration. Therefore, the information device 10A will be described in detail as an example.

As shown in FIG. 3, the information device 10A includes a processing unit 100A, a clocking unit 110A, a notification unit 120A, a communication unit 130A, a storage unit 140A, an acquisition unit 150, and an operation unit 160. However, in the configuration of the information device 10A, a part of these components may be deleted or changed, or another component may be added.

The processing unit 100A is made up of a CPU (central processing unit), DSP (digital signal processor), ASIC (application specific integrated circuit) or the like, for example. The processing unit 100A carries out various kinds of processing according to a program stored in the storage unit 140A and various commands inputted by the user via the operation unit 160. The processing by the processing unit 100A includes processing in which performance information is generated, based on information generated by the clocking unit 110A, the acquisition unit 150, and the operation unit 160, for example. The processing unit 100A also carries out processing in which the notification unit 120A reports performance information, processing in which the communication unit 130A sends and receives information to and from the outside, and the like.

The clocking unit 110A is made up of a real-time clock (RTC) IC or the like, for example, and generates and sends time information including the year, month, day, hour, minute, second or the like, to the processing unit 100A.

The notification unit 120A has a display unit 121, a sound notification unit 125, and a vibrating unit 127. The notification unit 120A reports performance information according to an instruction from the processing unit 100A.

Specifically, the display unit 121 gives a notification by displaying various images based on performance information, on the display screen 11 made up of an LCD (liquid crystal display), organic EL (electroluminescence) display, EPD (electrophoretic display), touch panel display or the like. The sound notification unit 125 gives a notification by outputting a sound based on performance information, from a speaker, buzzer or the like. The vibrating unit 127 gives a notification by generating various vibrations based on performance information.

The notification unit 120A need not necessarily have all of the display unit 121, the sound notification unit 125, and the vibrating unit 127, and may have a part of these or may have other notification measures.

The communication unit 130A has at least one transmitter/receiver conforming to a short-range wireless communication standard such as Bluetooth (trademark registered) (including BTLE (Bluetooth Low Energy)), Wi-Fi (Wireless Fidelity, trademark registered), Zigbee (trademark registered), NFC (near field communication), or ANT+ (trademark registered), for example, and sends and receives information to and from the external device 10B, 20, 30.

The storage unit 140A is made up of one or a plurality of IC memories, for example, and includes a ROM where programs are stored, and a RAM serving as a work area for the processing unit 100A. The RAM may include a non-volatile RAM. In the ROM or RAM, exercise/rest information acquired by the acquisition unit 150 and performance information generated by the processing unit 100A are stored.

The acquisition unit 150 has sensors which detect movements of a person, such as an acceleration sensor 151 and a water detection sensor 152, and acquires exercise/rest information when the athlete 2 carries out interval exercise. The acquisition unit 150 may further include a pulse wave sensor 153. In that case, the processing unit 100A extracts information such as pulse rate, based on pulse waves acquired by the pulse wave sensor 153.

The acceleration sensor 151 is a known MEMS sensor which detects acceleration in three axial directions that are substantially orthogonal to each other, for example. The acceleration sensor 151 outputs an acceleration signal that enables calculation of the gradient, the amount of movement or the like of the information device 10A. The amount of movement of the information device 10A can be calculated using the amount of change in the acceleration signal generated in each axial direction at the time of the movement. The acceleration signal as the output from the acceleration sensor 151 is sent to and processed by the processing unit 100A.

The water detection sensor 152 is a sensor which detects the information device 10A is in water.

The operation unit 160 has the buttons 12 (see FIG. 2), a key, a microphone, a touch panel, a speech recognition function or the like, for example, and sends an instruction from the user to the processing unit 100A as information.

Functional Configuration of External Device

As described above, the electronic device capable of managing performance information such as the information device 10B, the electronic display board 20, or the portable information terminal 30 functions as the external device 10B, 20, 30. As shown in FIG. 3, the external device 10B, 20, 30 has a processing unit 100B, a notification unit 120B, a communication unit 130B, and a storage unit 140B. The external device 10B, 20, 30 may also have a clocking unit 110B.

The processing unit 100B has functions equivalent to those of the processing unit 100A. Similarly, the clocking unit 110B has functions equivalent to those of the clocking unit 110A. The notification unit 120B has functions equivalent to those of the notification unit 120A. The communication unit 130B has functions equivalent to those of the communication unit 130A. The storage unit 140B has functions equivalent to those of the storage unit 140A.

The information device 10B, the electronic display board 20, or the portable information terminal 30, as the external device 10B, 20, 30, receives information sent from the information device 10A (for example, exercise/rest information and performance information or the like) via the communication unit 130B. The external device 10B, 20, 30 notifies the outside of the performance information based on the received information, via the notification unit 120B. At this time, the time information from the clocking unit 110B is used and the information or the like received from the information device 10A is stored in the storage unit 140B, according to need.

The database 80 is connected to the external device 10B, 20, 30 via a network, and stores exercise/rest information and performance information or the like, for example. The external device 10B, 20, 30 can acquire various kinds of information about training from the database 80. Although not shown in FIG. 3, the database 80 may be directly connected to the information device 10A via a network.

Generation of Performance Information

Figure 4:
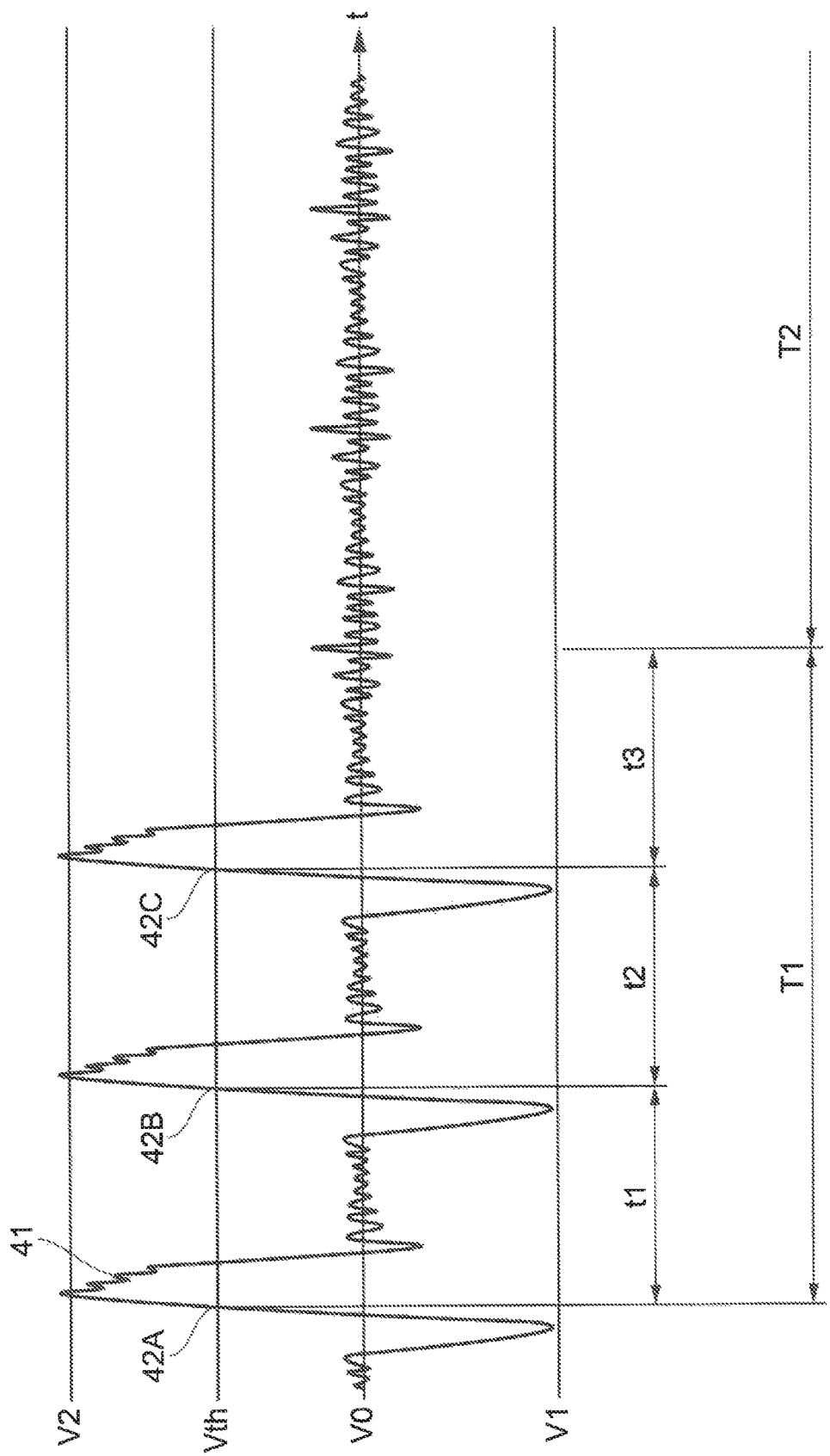
FIG. 4 shows an example of acceleration sensor output.

FIG. 4 shows an example of an output 41 from the acceleration sensor 151. Hereinafter, an example of a method for generating performance information from the output 41 will be described.

In FIG. 4, a horizontal axis t represents the passage of time, and the direction orthogonal to the horizontal axis t represents the magnitude (level) of the output 41. As shown in FIG. 4, the output 41 includes a time segment T1 in which the output level changes periodically between a peak level V1 on the negative side and a peak level V2 on the positive side, with the level V0 being a basis, and a time segment T2 in which the output level fluctuates around the level V0 without reaching the peak levels V1, V2. In FIG. 4, in order to avoid complexity in the illustration, the number of times the output 41 periodically changes in the time segment T1 is simplified to three.

The time segment T1 is the time during which the athlete 2 wearing the information device 10A carries out load exercise. The time segment T2 is the time during which the athlete 2 rests. In the example of FIG. 4, a threshold Vth is set between the level V0 and the level V2, and time points 42A, 42B, 42C when the output 41 crosses the threshold Vth (crosses the threshold from the negative side to the positive side, or reaches the threshold Vth or above) are thus detected.

Here, on the assumption that the time period between the time point 42A and the time point 42B is a time period t1 and that the time period between the time point 42B and the time point 42C is a time period t2, since there is no large difference in the action of the athlete in load exercise of interval exercise, the time period t1 and the time period t2 are of substantially the same length. Therefore, unless the output 41 crosses the threshold Vth around when a time period t3 which is of substantially the same length as the time period t1 and the time period t2 passes after the time point 42C, it is determined that the time segment T1 has finished and that the time segment T2 has begun. Thus, information of the length of the time segment T1, which is the time during which load exercise is carried out, is acquired.

If the output 41 crosses the threshold Vth in the time segment T2, it is determined that the time segment T2 has finished and that the time segment T1 has begun again. Thus, information of the length of the time segment T2, which is the time during which rest is carried out, is acquired.

The information about these various times is processed and generated by the processing unit 100A, 100B, based on the time information acquired from the clocking unit 110A, 110B.

As described above, the processing unit 100A, 100B can acquire the output 41 as exercise/rest information of the athlete 2 from the acceleration sensor 151 and generate performance information (that is, information about the lengths of the time segment T1 and the time segment T2, or the like).

Also, in interval exercise for swimming, for example, the number of times the output 41 crosses the threshold Vth indicates the number of strokes made in the time segment T1, during which the athlete 2 carries out load exercise. Therefore, the processing unit 100A, 100B can report the number of strokes made in swimming, as a part of performance information.

Operation of Performance Information Notification Device

Figure 5:
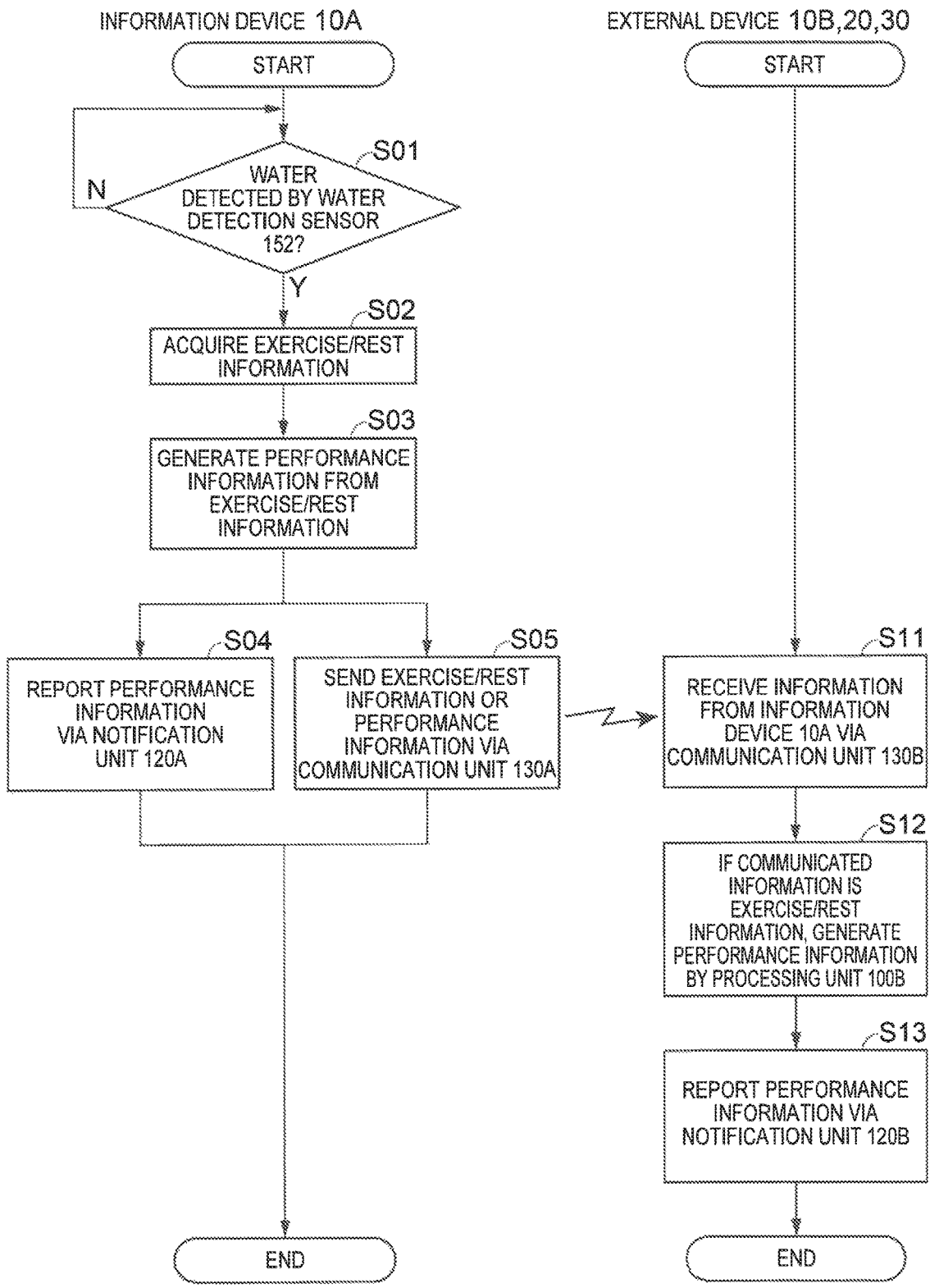
FIG. 5 is a flowchart showing an example of a method for controlling the performance information notification device.

Next, referring to FIGS. 3 and 4, the operations of the information device 10A and the external device 10B, 20, 30 as performance information notification devices will be described. FIG. 5 is a flowchart showing an example of a method for controlling performance information notification devices. More specifically, FIG. 5 is a flowchart executed by the processing devices 100A, 100B according to programs stored in the storage units 140A, 140B when interval exercise for swimming is carried out, and a flowchart showing an example of a performance information notification method as well. Hereinafter, the operations of the performance information notification devices will be described, based on the flowchart of FIG. 5.

Step S01: The processing unit 100A of the information device 10A checks whether water is detected by the water detection sensor 152 of the information device 10A worn by the athlete 2 or not. If water is not detected by the water detection sensor 152 (N in Step S01), the state of the water detection sensor 152 continues to be checked. Meanwhile, if water is detected by the water detection sensor 152 (Y in Step S01), the processing shifts to Step S02.

Step S02: The processing unit 100A determines that the athlete 2 is in water, and acquires the output 41 from the acceleration sensor 151 as exercise/rest information. Also, the processing unit 100A may acquire the output 41 from the acceleration sensor 151 by having the operation unit 160 operated, instead of determining that the athlete 2 is in water, based on the result of detection by the water detection sensor 152.

Step S03: The processing unit 100A generates performance information such as information about the lengths of the time segment T1 and the time segment T2 from the output 41 by the foregoing processing.

Step S04: The processing unit 100A notifies the outside of the generated performance information via the notification unit 120A with a display, notification sound, vibration or the like.

Step S05: The processing unit 100A sends the acquires exercise/rest information (output 41) or the generated performance information to the external device 10B, 20, 30 via the communication unit 130A. In the case of sending the acquired exercise/rest information (output 41) to the external device 10B, 20, 30, the processing may proceed from Step S02 to Step S05, skipping Step S03.

Step S11: The processing unit 100B of the external device 10B, 20, 30 receives the output 41 as the exercise/rest information or the performance information from the information device 10A, via the communication unit 130B.

Step S12: If the received information is the output 41, the processing unit 100B generates the performance information such as the information about the lengths of the time segment T1 and the time segment T2 from the output 41, as described above.

Step S13: The processing unit 100B notifies the outside of the received or generated performance information via the notification unit 120B with a display, notification sound, vibration or the like. If the information received from the information device 10A is the performance information generated in the information device 10A, the received performance information may be reported as it is.

Advantageous Effects

As described above, according to the embodiment, the performance information notification device acquires information (exercise/rest information) indicating at least one of load exercise and rest in interval exercise. The performance information notification device can also notify the outside of information (performance information) about at least one of the time during which the load exercise is carried out and the time during which the rest is carried out in the interval exercise, based on the exercise/rest information, via a screen display, notification sound, vibration or the like. Therefore, information during training by interval exercise of the athlete 2 is acquired, and with the notification from the performance information notification device, the athlete 2 can easily learn information about the training even during the training.

Also, the information device 10A, having the acquisition unit 150 and the notification unit 120A, can independently carry out the acquisition of exercise/rest information and the notification of performance information. Therefore, the information device 10A can independently function as the performance information notification system 1, and the athlete 2 can check the performance information of his/her own interval exercise in real time, wearing the information device 10A on the wrist, for example.

Also, the performance information notification system 1 has the communication unit 130A and the communication unit 130B, and information can be communicated between the communication unit 130A and the communication unit 130B. Therefore, the acquisition unit 150 acquiring exercise/rest information and the notification unit 120B reporting performance information may be installed in places distant from each other. That is, the information device 10A having the acquisition unit 150 and the communication unit 130A can be worn by the athlete 2, and information can be sent and reported from the information device 10A to the external device 10B, 20, 30 having the notification unit 120B and the communication unit 130B. As a result, for example, if each of the coach 3 and the athlete 2 has the same information device 10 (10A or 10B), the coach 3 can learn the same information by the same notification method as the athlete 2. Meanwhile, if the external device 10B, 20, 30 is the electronic display board installed on the poolside, for example, performance information is displayed and reported on a large screen that is easy to see, on the electronic display board 20. If the external device 10B, 20, 30 is the portable information terminal 30 such as a smartphone or tablet carried by the coach 3, for example, performance information can be processed, using application software of the potable information terminal 30.

Modifications

While the embodiment of the invention is described above, various modifications can be made without departing from the scope of the invention such as follows. The same configurations as those in the embodiment are denoted by the same reference signs and are not described further in detail.

Modification 1

In the embodiment, the information device 10A has the notification unit 120A, the communication unit 130A, and the acquisition unit 150. However, the notification unit 120A may be omitted. That is, the notification of performance information to the outside need not be carried out by the information device 10A itself. The information can be sent from the communication unit 130A, and the external device 10B, 20, 30 receiving the information can carry out the notification. Also, the information device 10A may send exercise/rest information acquired by the acquisition unit 150 to the external device 10B, 20, 30 without generating performance information in the processing unit 100A, and the processing unit 100B of the external device 10B, 20, 30 may generate performance information. Thus, since the components of the information device 10A can be simplified, the information device 10A can be made smaller, lighter, and easier to wear, and a reduction in electricity consumption can be achieved as well.

Modification 2

In the embodiment, the information device 10A is a wrist-worn electronic device having the band 13 and worn around the wrist of the athlete 2. However, the information device 10A may also be a chest belt-type electronic device worn around the chest. According to this configuration, the electronic device can be provided with a heart rate sensor. The notification unit can report heart rate information detected by the heart rate sensor, along with performance information. The heart rate information and other information about exercise are examples of performance information.

Modification 3

Before interval exercise is carried out, the information about the time during which the load exercise is carried out and the time during which the rest is carried out, inputted from the outside by an operation on the operation unit 160, may be stored in the storage unit 140A. The information device 10A may compare the performance information after the interval exercise with the stored input information, and report the difference between these. According to this configuration, the user can learn the difference between planned interval exercise and executed interval exercise, by storing the planned interval exercise in the information device 10A in advance. Therefore, the quality of training can be improved.

Next, the form of display on the performance information notification device in the performance information notification system 1 will be described. Specifically, a modification of the form of display of performance information displayed on the display screen 11 of the information device 10 (10A or 10B), the display screen 21 of the electronic display board 20, or the display screen 31 of the portable information terminal 30 will be described.

Modification 4

Figure 6:
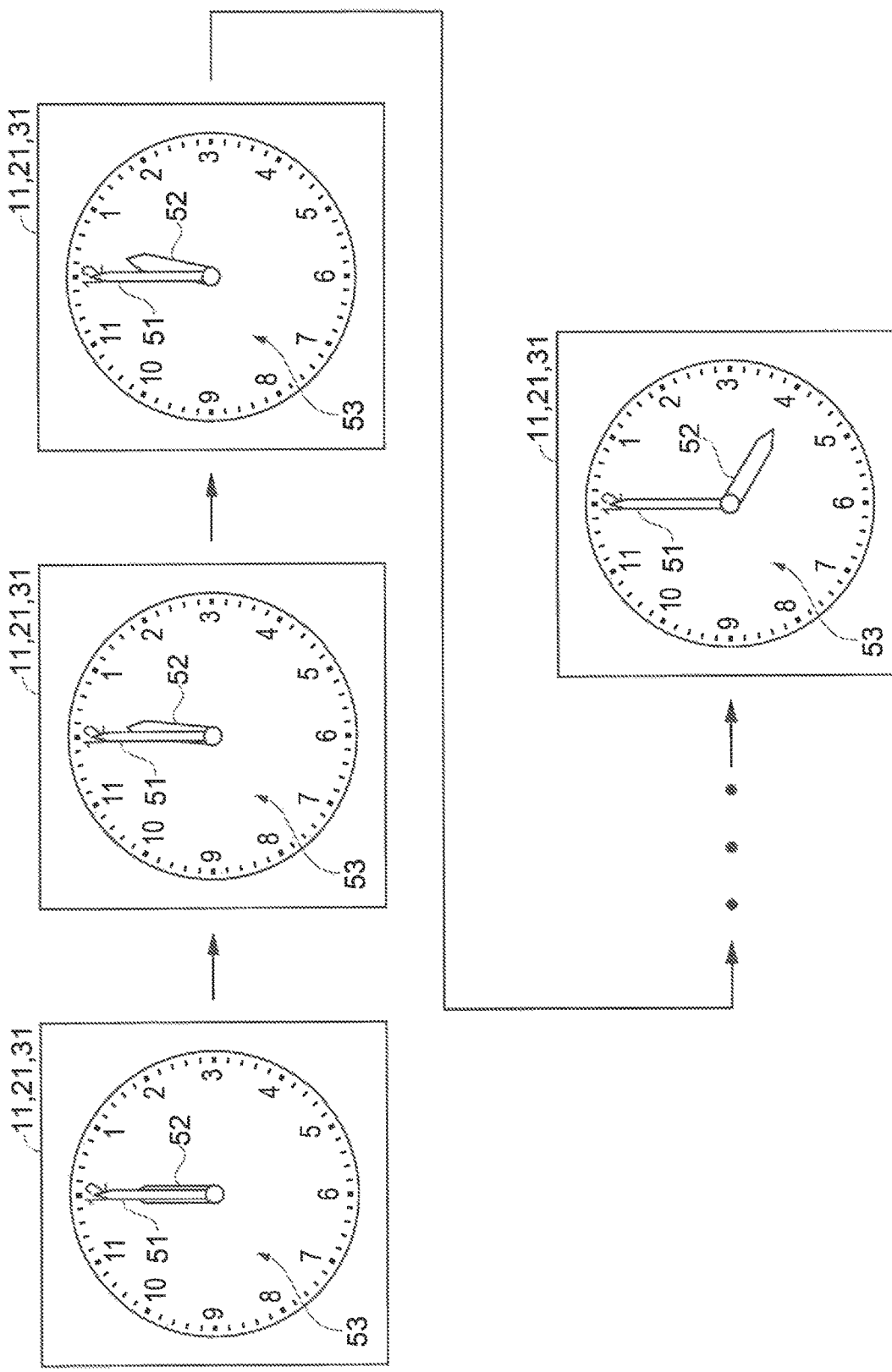
FIG. 6 shows an example of display on the performance information notification device.

FIG. 6 shows an example of display on the performance information notification device. As performance information, the time during which load exercise is carried out in one period of exercise cycle and the number of times the exercise cycle is carried out are displayed. FIG. 6 is also a transition chart showing the way the display of a circular analog display-type timer shifts as the number of times exercise cycle increases. This analog display-type timer has a clock face 53 where black spots are arranged at 60 positions equally dividing the circumference and where numerical values are arranged at 12 positions equally dividing the circumference, similarly to a common analog display clock. On the clock face 53, a minute hand 51 and an hour hand 52 shows performance information.

In FIG. 6, the circular analog display-type timer, with both the minute hand 51 and the hour hand 52 pointing at the position of the $12^{th}$ hour, is the initial state of the transition chart. This is the display when interval exercise begins. In the circular analog display-type timer, the minute hand 51 makes a round over one period of exercise cycle, indicating the time elapsed. Therefore, by checking the position of the minute hand 51 when the load exercise is finished, the user can learn the time during which the load exercise is carried out and the time of rest until the next exercise cycle begins, as performance information.

The hour hand 52 indicates the number of time the exercise cycle is carried out. Therefore, in the second state in the transition chart, the minute hand 51 points at the position of the $12^{th}$ hour and the hour hand 52 points at the first black spot, indicating that the first exercise cycle is finished. Similarly, in the third state of the circular analog display-type timer in the transition chart, the hour hand 52 points at the second black spot, indicating that the second exercise cycle is finished. In the last state of the circular analog display-type timer, the hour hand 52 points at the $20^{th}$ black spot, indicating that the $20^{th}$ exercise cycle is finished.

Thus, according to this example of display, the athlete 2 can learn performance information, based on the positions of the minute hand 51 and the hour hand 52. Also, since it can be understood at a glance that the next exercise cycle is started as the minute hand 51 reaches the position of the $12^{th}$ hour, the athlete 2 can anticipate the timing of starting the next exercise cycle and can easily pay attention not to delay the start of the next exercise cycle. Moreover, since the hour hand 52 indicates the number of times of exercise cycle, the user need not count and remember the number of times of exercise cycle during training.

Modification 5

Figure 7A:
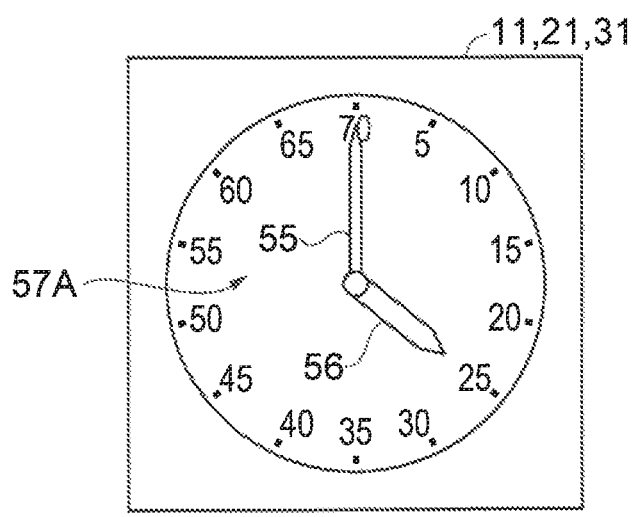
FIG. 7A shows another example of display on the performance information notification device.
Figure 7B:
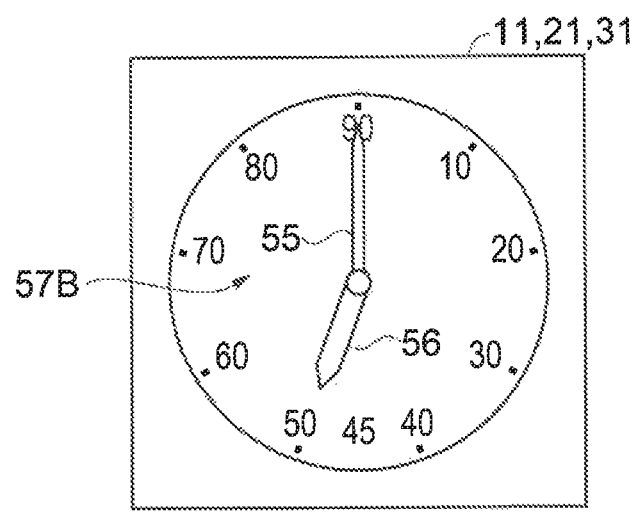
FIG. 7B shows another example of display on the performance information notification device.

FIGS. 7A and 7B show other examples of display on the performance information notification device. As performance information, the time during which load exercise is carried out in one period of exercise cycle and the number of time the exercise cycle is carried out are displayed. In the circular analog display-type timers in FIGS. 7A and 7B, a minute hand 55 makes a round over one period of exercise cycle, indicating the time elapsed, as in the example of display in FIG. 6. Also, an hour hand 56 indicates the number of times the exercise cycle is carried out.

The difference of the examples of display in FIGS. 7A and 7B from the example of display in FIG. 6 is that one period of exercise cycle is evenly distributed on clock faces 57A, 57B, and that the numerical value of the one period is displayed at the position corresponding to the position of the $12^{th}$ hour in the example of display in FIG. 6. Specifically, in the example of display in FIG. 7A, 70 seconds, which is one period, is displayed at the position of the $12^{th}$ hour, and the hour hand 56 points at 25, indicating that 25 exercise cycles are finished. In the example of display in FIG. 7B, 90 seconds, which is one period, is displayed at the position of the 12$^{th}$ hour, and the hour hand 56 points at 50, indicating that 50 exercise cycles are finished.

According to these examples of display, since one round on the clock faces 57A, 57B is expressed in the form of the numerical value indicating one period of exercise cycle, there is an advantage that performance information can easily be read from the position of the minute hand 55, in addition to advantageous effects similar to those of the example of display in FIG. 6.

Modification 6

Figure 8:
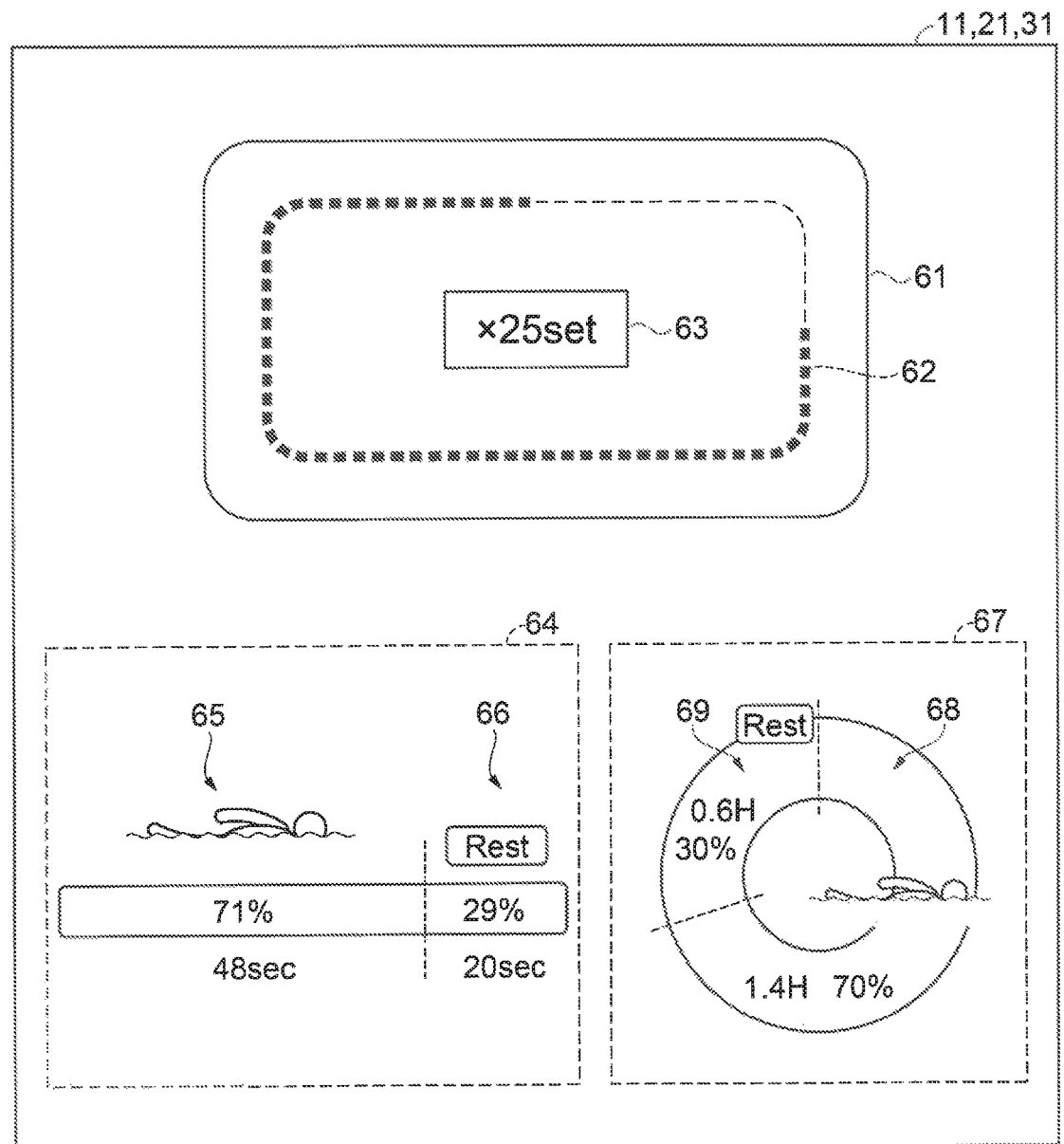
FIG. 8 shows another example of display on the performance information notification device.

FIG. 8 shows another example of display on the performance information notification device. In this example of display, a subtraction timer 61, a bar chart in a bar chart area 64, and a pie chart in a pie chart area 67 on the display screen 11, 21, 31 display performance information.

The subtraction timer 61 displays the time during which load exercise is carried out in one period of exercise cycle and the number of times the exercise cycle is carried out, as performance information. In the subtraction timer 61, a circle formed by display segments 62 in a number corresponding to one period of exercise cycle is displayed. When the exercise cycle begins, all of the display segments 62 are lit. As the time of load exercise passes after the exercise cycle begins, the display segments 62 are sequentially switched off accordingly and the number of lit display segments 62 gradually decreases. Therefore, the user can learn performance information, based on the number of display segments 62 that are lit or switched off. Also, since the timing when all of the display segments 62 are switched off is the timing of starting the next exercise cycle, the athlete 2 can anticipate the timing of starting the next exercise cycle and can easily pay attention not to delay the start of the next exercise cycle.

Moreover, in a center part 63 of the circle of the display segments 62, the number of times of exercise cycle is displayed, and the numerical value decreases by 1 eve time one exercise cycle is finished. Therefore, the user can easily learn the remaining number of times of exercise cycle.

In the bar chart area 64, the time during which load exercise is carried out in one period of exercise cycle and the proportion of the time during which the load exercise is carried out to the one period of exercise cycle (second proportion of exercise) are displayed, as performance information. Also, in the bar chart area 64, the time during which rest is carried out in the one period of exercise cycle and the proportion of the time during which the rest is carried out to the one period of exercise cycle (second proportion of rest) are displayed in the form of a bar chart and numerical value, as performance information.

Specifically, in this example of display, one period of exercise cycle is 68 seconds, and the time during which load exercise is carried out (48 sec) in the one period of exercise cycle and the second proportion of exercise by the percentage (71%) are displayed in an area 65. Similarly, in an area 66, the time during which rest is carried out (20 sec) and the second proportion of rest by the percentage (29%) are displayed. Also, the bar chart is divided into two parts of display, corresponding to the proportion of the time during which the load exercise is carried out and the proportion of the time during which the rest is carried out. Therefore, the user can intuitively learn the difference in length between the time during which the load exercise is carried out and the time during which the rest is carried out.

In the pie chart area 67, the cumulative value of the time during which load exercise is carried out (cumulative time of exercise) in one session of interval exercise and the proportion of the cumulative time of exercise to the time during which the one session of interval exercise is carried out (first proportion of exercise) are displayed as performance information. Also, in the pie chart area 67, the cumulative value of the time during which rest is carried out (cumulative time of rest) in the one session of interval exercise and the proportion of the cumulative time of rest to the time during which the one session of interval exercise is carried out (first proportion of rest) are displayed as performance information.

Specifically, in the pie chart area 67, a pie chart showing the cumulative time of exercise and the cumulative time of rest is displayed. In a part 68 of the pie chart, the cumulative time of exercise (1.4 H) and the first proportion of exercise by the percentage (70%) are shown. Similarly, in a part 69, the cumulative time of rest (0.6 H) and the first proportion of rest by the percentage (30%) are shown. Also, the pie chart is divided into two parts of display corresponding to the first proportion of exercise and the first proportion of rest. Therefore, the user can intuitively learn the proportion of the length of the time during which the load exercise is carried out and the length of the time during which the rest is carried out. Also, the user can grasp the intensity of exercise and the physical load of the training carried out by the user him/herself in one session of interval exercise, based on the cumulative time of exercise and the cumulative time of rest.

The above three examples of display of performance information need not be displayed at the same time on the same screen and may be displayed separately. Also, the first proportion of exercise, the second proportion of exercise, the first proportion of rest, and the second proportion of rest may be expressed by the permillage instead of the percentage.

Modification 7

Figure 9:
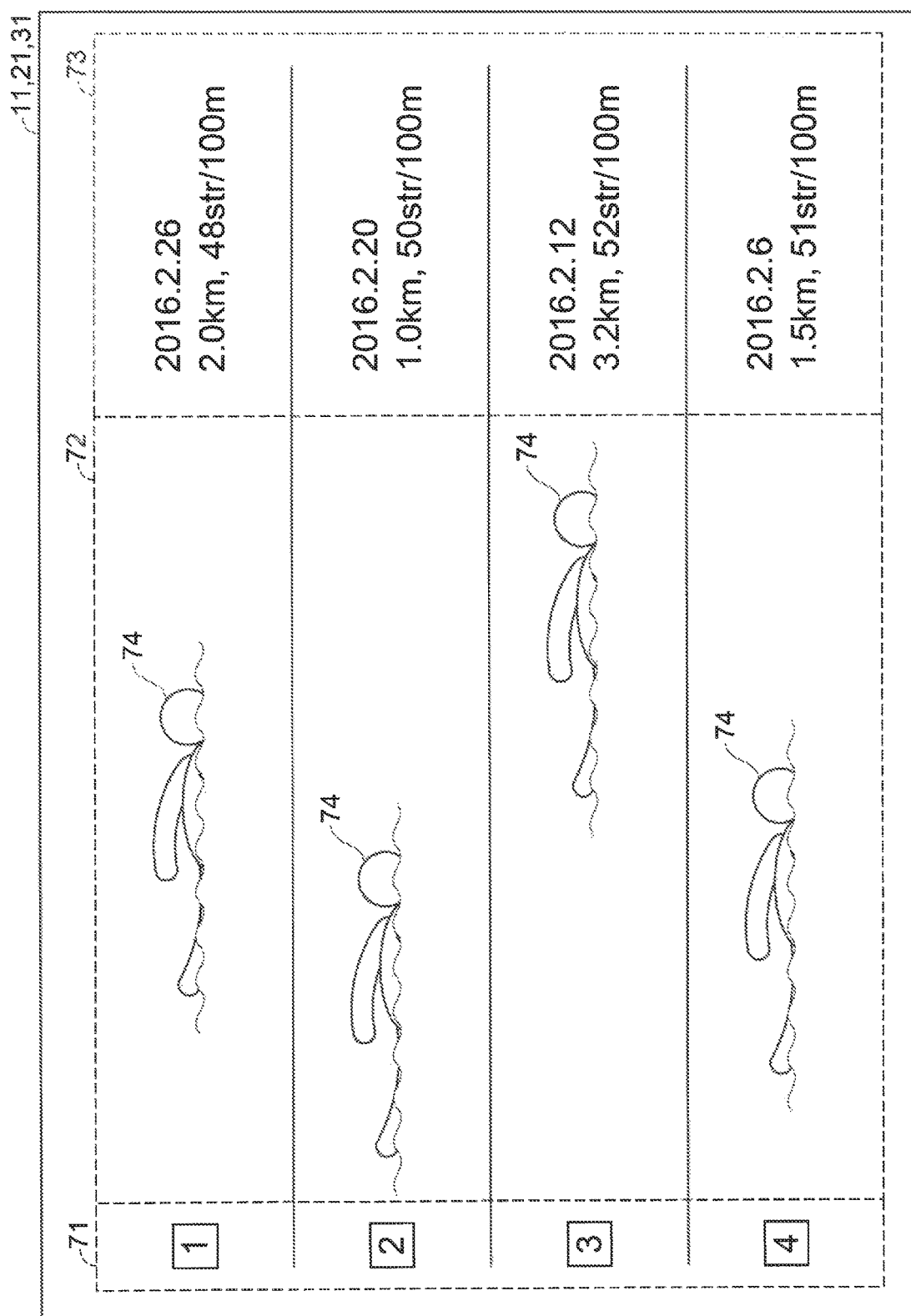
FIG. 9 shows another example of display on the performance information notification device.

FIG. 9 shows another example of display on the performance information notification device. In this example of display, date information, distance information, stroke information or the like is displayed on the display screen 11, 21, 31 as performance information for each interval exercise. Specifically, the number of each interval exercise is shown in an area 71. Performance information is shown by an icon 74 in an area 72. Performance information is shown by a numerical value in an area 73.

As for the number of each interval exercise in the area 71, the smallest number indicates the last interval exercise (that is, the interval exercise that is immediately before). As the numerical value increases by 1, it indicates the interval exercise that is immediately before the last interval exercise. However, the way of assigning the numbers is not limited to this and may be arbitrary.

The position of display of the icon 74 in the area 72 on the display screen 11, 21, 31 indicates the extent to which the load exercise is carried out by the athlete 2. In this example of display, this corresponds to the distance the athlete 2 swims. Specifically, as shown in the area 73, the distance the athlete 2 swims is 2.0 km, 1.0 km, 3.2 km, and 1.5 km in the ascending order of the number of interval exercise. The icon 74 is displayed farther from the area 71 in the longitudinal direction as the distance he distance the athlete 2 swims becomes longer. Therefore, the user can intuitively compare and learn the intensities of a plurality of interval exercises.

In the area 73, performance information for each interval exercise is displayed in the form of numerical values. Specifically, the date when the interval exercise is carried out, the distance swum, and the average number of strokes per unit distance (100 m) are displayed. Therefore, the user can specifically learn the intensities of a plurality interval exercises from the numerical values. However, the displayed performance information is not limited to this and may be arbitrary.

Modification 8

FIG. 10 shows another example of display on the performance information notification device. In this example of display, the time during which load exercise is carried out, the time during which rest is carried out, and stroke information or the like, in one period of exercise cycle, are displayed on the display screen 11, 21, 31 as performance information for each exercise cycle. Specifically, the number of each exercise cycle is shown in an area 81. In an area 82, the time during which load exercise is carried out and the time during which rest is carried out are displayed for each exercise cycle (area 86), as performance information. A boundary position 87 between the load exercise and the rest may shift to the left and right, for example, depending on the proportion of the times of these. In an area 83, the number of strokes is shown for each exercise cycle. Therefore, the user can check the performance information for each exercise cycle and learn how the performance information changes. An icon 84 indicates that it is an area showing the time during which load exercise is carried out. An icon 85 indicates that it is an area showing the time during which rest is carried out.

Modification 9

Figure 11A:
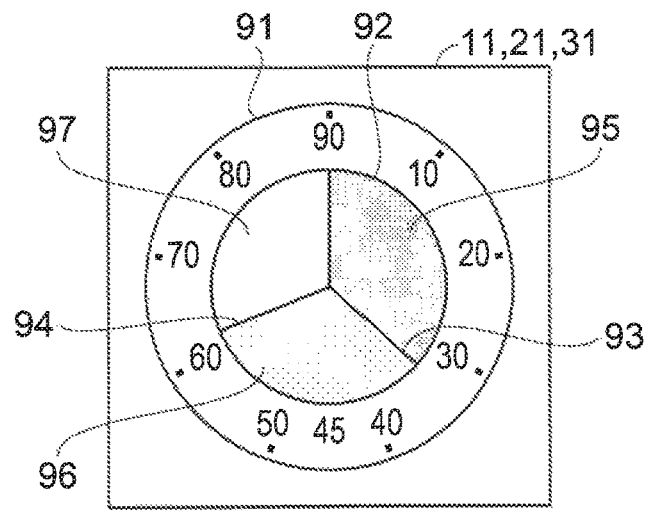
FIG. 11A shows another example of display on the performance information notification device.

FIG. 11A shows another example of display on the performance information notification device. In this example of display, a pie chart showing the time during which load exercise is carried out and the time during which rest is carried out, in one period of exercise cycle, is displayed on the display screen 11, 21, 31 as performance information for each exercise cycle. In the pie chart, one period of exercise cycle is displayed in the form of numerical values (in FIG. 11A, 90 seconds) between an outer circle 91 and an inner circle 92. Inside the inner circle 92, a segment 95 and a segment 96 indicating the lapse of time are displayed. The segment 95 indicates the time during which load exercise is carried out. The segment 96 indicates the time during which rest is carried out. That is, a boundary line 93 between the segment 85 and the segment 96 indicates the time during which the load exercise is carried out (in FIG. 11A, 32 seconds). Also, a boundary line 94 between the segment 96 and a segment 97 moves clockwise toward the position of 90 seconds with the lapse of time, and indicates the time elapsed, taken for carrying out the rest after carrying out the load exercise. FIG. 11A shows that the load exercise is carried out for 32 seconds and that the rest is subsequently carried out up to the current point of 61 seconds.

According to this example of display, the user can check the time during which load exercise is carried out, by checking the position of the segment 95 or the boundary line 93 after finishing the load exercise. Also, the user can check the time taken for rest and the time until the next exercise cycle begins, by checking the position of the segment 96 or the boundary line 94. Therefore, the athlete 2 can easily pay attention not to delay the start of the next exercise cycle.

Modification 10

Figure 11B:
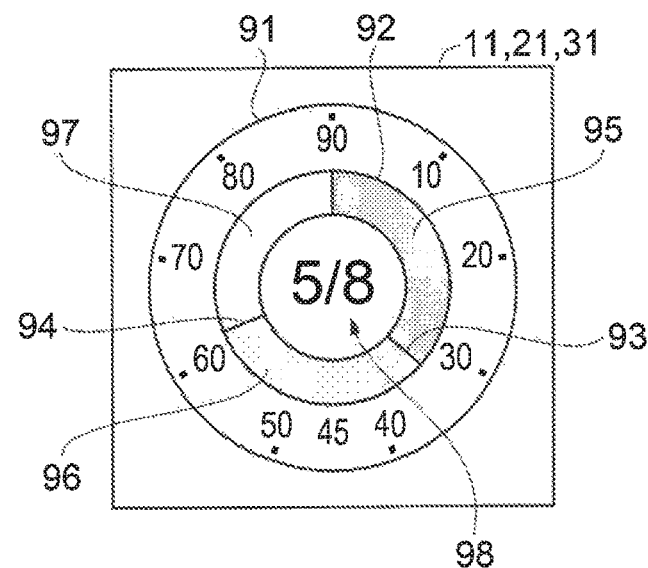
FIG. 11B shows another example of display on the performance information notification device.

FIG. 11B shows another example of display on the performance information notification device. In this example of display, a center part 98 is arranged in the area where the segments 95, 96, 97 of the pie chart in the example of display in FIG. 11A are displayed. The components except for the center part 98 are similar to those in the example of display in FIG. 11A and therefore are denoted by the same reference signs and not described further in detail. In the center part 98, information about the number of times of exercise cycle is displayed. Specifically, in addition to the example of display in FIG. 11A, the number of times the exercise cycle is to be carried out and the number of times the exercise cycle is finished are displayed as performance information.

According to this example of display, the user can easily learn the remaining number of times of exercise cycle, in addition to the advantageous effects of the example of display in FIG. 11A. Also, as the information about the number of times of exercise cycle, the remaining number of times of exercise cycle may be displayed instead of the number of times the exercise cycle is finished.

Modification 11

Figure 12:
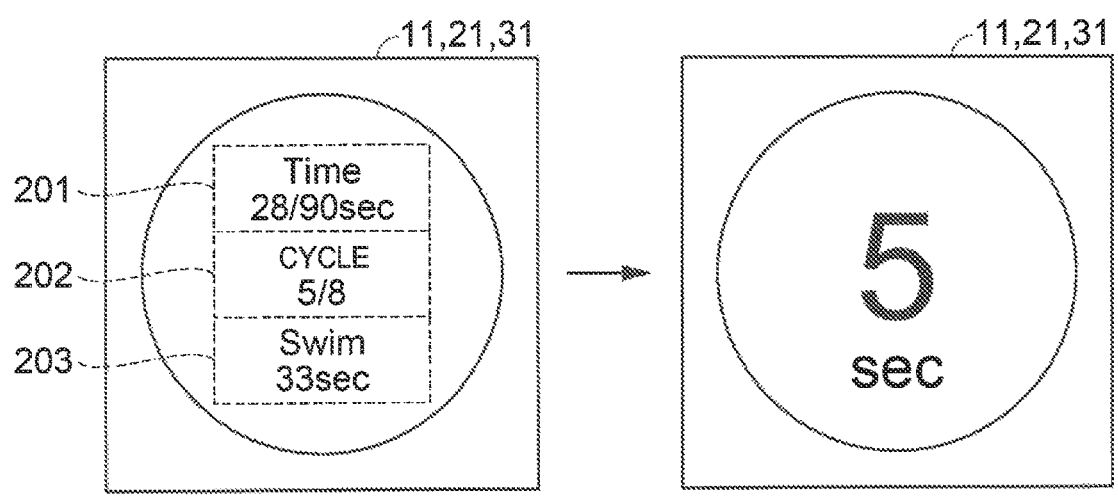
FIG. 12 shows another example of display on the performance information notification device.

FIG. 12 shows another example of display on the performance information notification device. In this example of display, the remaining time of one period of exercise cycle, the number of times of exercise cycle, and the time during which load exercise is carried out in the one period of exercise cycle are displayed in the form of numerical values on the display screen 11, 21, 31 as performance information. Information about the time of the exercise cycle is displayed in an area 201. Information about the number of times of exercise cycle is displayed in an area 202. The time during which load resistance information is carried out is displayed in an area 203.

Specifically, in the area 201 in FIG. 12, it is shown that the remaining time is 28 seconds, out of one period of exercise cycle of 90 seconds. In the area 202, it is shown that the number of times the exercise cycle is to be carried out is 8 and that 5 exercise cycles are finished. In the area 203, it is shown that the time during which the load exercise is carried out is 33 seconds. Also, when the remaining time of the one period of exercise cycle reaches a predetermined value (in FIG. 12, 5 seconds), the display changes to show the remaining time only and countdown is then performed until remaining time becomes 0.

According to this example of display, the user can check the time during which load exercise is carried out in the exercise cycle. Also, since the remaining time of one period of exercise cycle can be checked in the same way as a countdown timer, the athlete 2 can easily pay attention not to delay the start of the next exercise cycle.

Modification 12

Figure 13:
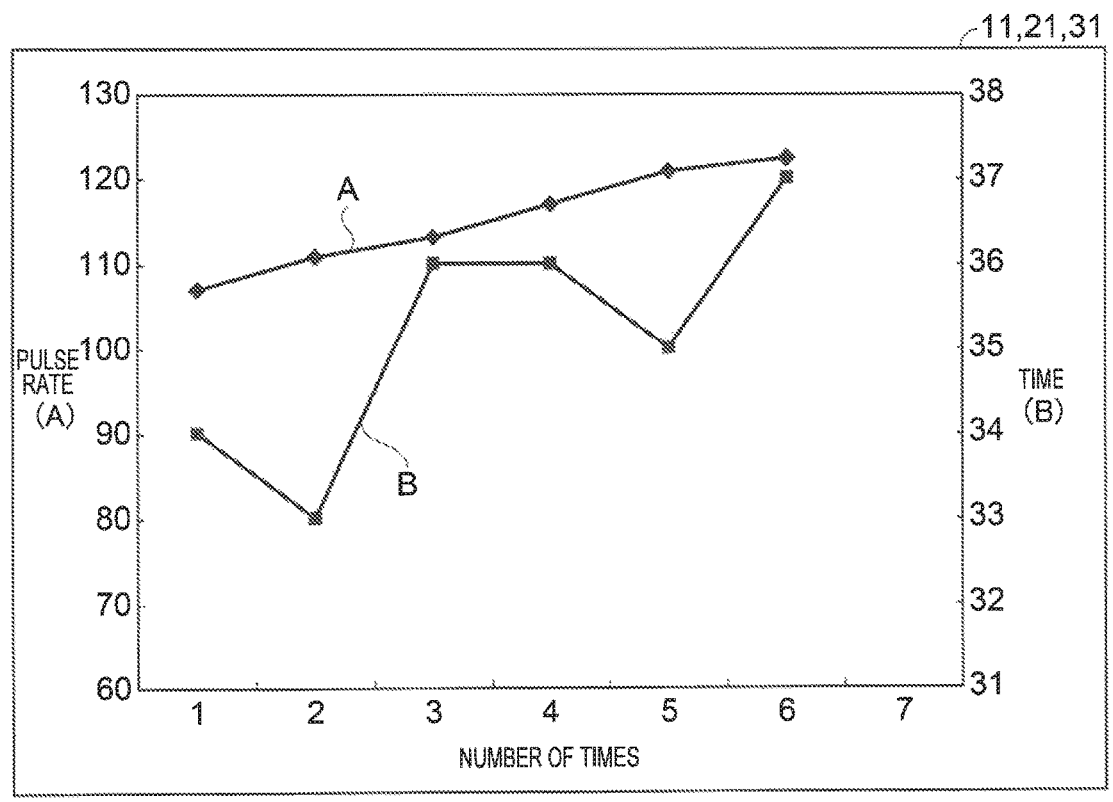
FIG. 13 shows another example of display on the performance information notification device.

FIG. 13 shows another example of display on the performance information notification device. In this example of display, the pulse rate of the athlete 2 and the time during which load exercise is carried out in one period of exercise cycle are displayed in the form of a line graph on the display screen 11, 21, 31 as performance information. The horizontal axis of the graph represents the number of each exercise cycle. One vertical axis (A) represents the maximum pulse rate during the exercise cycle. The other vertical axis (B) represents the time during which load exercise is carried out in one period of exercise cycle. As shown in the example of display of FIG. 13, the graph includes a line A and a line B, both indicating performance information. The line A indicates the maximum pulse rate of the athlete 2 during each exercise cycle. The line B indicates the time during which load exercise is carried out in each exercise cycle.

According to this example of display, the user can learn the intensity of the exercise in the exercise cycle and the load on the cardiopulmonary function at the time, from the maximum pulse rate. Also, since the performance information including the maximum pulse rate in each exercise cycle is connected by the line, the user can easily check changes in the performance information in the exercise cycle, from the shape of the line.

Other Modifications

As other forms of display of performance information, a preset target value and result, a predicted value derived from history and result, a maximum value, minimum value and average value or the like may be displayed in juxtaposition. Also, the display may be changed when an item of performance information satisfies a predetermined condition. For example, a change to the display may be made, such as changing colors (highlight by reversing black and white or by using a different character color or background color, or the like), changing display modes (a predetermined mark is displayed, characters are blinked, characters larger than those used in normal display are used, or the like), or the like.

In the above embodiment and modifications, the information device 10 (10A or 10B) is illustrated as an electronic device worn around the wrist of the user or as a chest belt-type electronic device. However, the site on the body where the information device 10 (10A or 10B) is worn can be changed according to need. For example, an electronic device which is to be worn around the upper arm of the user with the band 13 may be employed. Alternatively, an electronic device worn on the head with the band 13 like goggles may be employed. The information device 10 (10A or 10B) is not limited to wristwatch-type and may be tablet-type, action camera-type, or goggle-type. Also, an eyeglass-type device made up of the information device 10 (10A or 10B) provided on an eyeglass temple-like structure instead of the band 13 may be employed. Alternatively, an earphone-type, ring-type or pendant-type electronic device, an electronic device mounted on sports equipment, or a smartphone, head-mounted display (HMD), head-up display (HUD), or the like may be employed as well.

Detecting turns in swimming with the use of the acceleration sensor 151 is known. Therefore, if the information device 10A is used in a competition pool and this turn detection measure is utilized, the performance information notification device can notify the outside of the distance the athlete 2 swims, based on the number of turns made and the length of the pool.

The performance information notification device may also have a function which allows the user to input the type of load exercise before or after carrying out interval exercise. For example, in the case of swimming, a swimming stroke such as crawl, breaststroke, butterfly, or backstroke may be inputted and recorded along with the performance information of interval exercise in the storage unit 140A, 140B as a history.

Alternatively, a swimming stroke determined using a known swimming stroke detection technique or the like may be recorded along with the performance information of interval exercise in the storage unit 140A, 140B as a history.

In the above embodiment and modifications, the sensor used in the acquisition unit 150 is the acceleration sensor 151, the water detection sensor 152, and the pulse wave sensor 153. However, the sensor used is not limited to these. For example, the acquisition unit 150 may include a pressure sensor, gyro sensor, velocity sensor, angular velocity sensor, altitude sensor, temperature (atmospheric temperature, body temperature) sensor, geomagnetic sensor, ultraviolet sensor, perspiration sensor, blood pressure sensor, $SpO_2$ (blood oxygen concentration) sensor, lactic acid sensor, blood sugar sensor or the like.

The information device 10 (10A or 10B) may use a GNSS (Global Navigation Satellite System) such as the GPS (Global Positioning System). For example, one or two or more of satellite positioning systems such as the EGNOS (European Geostationary-Satellite Navigation Overlay Service), QZSS (Quasi Zenith Satellite System), GLONASS (GLObal NAvigation Satellite System), GALILEO, and BeiDou (BeiDou Navigation Satellite System) may be used. Also, as at least one of the satellite positioning system, a SBAS (Satellite-Based Augmentation System) such as the WAAS (Wide Area Augmentation System) or EGNOS (European Geostationary-Satellite Navigation Overlay Service) may be used.

Thus, the amount of movement, moving speed or the like of the athlete 2 may be detected and reported as performance information.

The acquisition unit 150 and the processing unit 100A, 100B may acquire or generate at least one of the pace of load exercise of the athlete 2 in interval exercise, cumulative distance, speed, lap time, calories burned, duration of exercise, heart rate, time during which exercise is done within a predetermined heart rate zone, time taken to achieve a predetermined heart rate zone, $VO_2Max$ (maximum oxygen uptake), predicted time, predicted distance, and $SpO_2$ (blood oxygen concentration). The acquired or generated information may be reported as performance information.

The application of the information device 10 (10A or 10B) and the performance information notification system1 is not limited to interval exercise and swimming. In various kinds of exercise, the acquisition unit 150 and the processing unit 100A, 100B may acquire or generate the pace of load exercise of the athlete 2, cumulative distance, stride, pitch, number of steps taken, speed, lap time, split time, number of steps taken per lap, calories burned, duration of exercise, cumulative altitude ascent, cumulative altitude descent, elevation above sea level, gradient, heart rate, time during which exercise is done within a predetermined heart rate zone, time taken to achieve a predetermined heart rate zone, $VO_2Max$ (maximum oxygen uptake), predicted time, predicted distance, $SpO_2$ (blood oxygen concentration), amount of perspiration, and water intake. The acquired or generated information may be reported as performance information.

The information device 10 (10A or 10B) and the performance information notification system 1 may also have an amount of activity meter function. The acquisition unit 150 and the processing unit 100A, 100B may acquire or generate at least one of the duration of exercise, calories burned, number of steps taken, hours of sleep, stress level (being excited or relaxed, or active state of sympathetic nerves and parasympathetic serves), number of steps taken in brisk walk, number of steps taken in running, number of floors climbed in a building, number of stairs climbed, waist measurement, heart rate, stride, distance, sleeping state, amount of perspiration, and water intake, as a parameter of the amount of activity.

The information device 10 (10A or 10B) may also taken in calorie intake, body weight and the like via the operation unit 160 and the communication unit 130A, 130B.

The performance information notification system 1 is not limited to swimming and can also be applied to running, walking, cycling, trail running, mountain climbing, trekking, triathlon, skiing (including cross-country skiing, ski jumping and the like), snowboarding, snowshoe hiking, skating or the like.

In the above embodiment and modifications, the information device 10B, the electronic display board 20, or the portable information terminal 30 acquires exercise/rest information or performance information or the like from the information device 10A. However, the source from which the information is acquired is not limited to this. For example, the information device 10B, the electronic display board 20, or the portable information terminal 30 may acquire exercise/rest information measured by another electronic device (not shown) via the network NW, then generate performance information based on the acquired information, and notify the outside of the performance information. In this case, the communication unit 130B includes the function of acquiring exercise/rest information (acquisition unit).

The above embodiment and modifications are examples and not limiting. For example, the embodiment and modifications can be suitably combined.

The invention also includes configurations substantially the same as the configurations described in the embodiment (for example, configurations with the same function, method and result, or configuration with the same objective and advantage effect). The invention also includes configurations formed by replacing non-essential parts of the configurations described in the embodiment. The invention also includes configurations which can achieve the same advantageous effects as the configurations described in the embodiment, or configurations which can achieve the same objectives as the configurations described in the embodiment. The invention also includes configurations formed by adding known techniques to the configurations described in the embodiment. Moreover, suitable changes can be made without departing from the scope of the invention.

The entire disclosure of Japanese Patent Application No. 2016-063265, filed Mar. 28, 2016 is expressly incorporated by reference herein.

What is claimed is:

1. A performance information notification device comprising a processor configured to:
    acquire information about at least one exercise cycle detected by a sensor, the at least one exercise cycle including a load exercise session and a rest session; and
    report performance information about a time during which the load exercise session is carried out in proportional relation to a time during which the rest session is carried out, based on the acquired information.

2. The performance information notification device according to claim 1, wherein
    the performance information includes at least one of a cumulative value of the time during which the load exercise session is carried out and a cumulative value of the time during which the rest session is carried out.

3. The performance information notification device according to claim 1, wherein
    the performance information includes at least one of a proportion of a cumulative value of the time during which the load exercise session is carried out to a total time of the exercise cycle, and a proportion of a cumulative value of the time during which the rest session is carried out to the total time of the exercise cycle.

4. The performance information notification device according to claim 1, wherein
    the performance information includes at least one of a time during which the load exercise session is carried out in the one exercise cycle and a time during which the rest session is carried out in the one exercise cycle.

5. The performance information notification device according to claim 1, wherein the sensor detects a movement of a person.

6. The performance information notification device according to claim 1, further comprising
    a clock that measures a time elapsed,
    wherein the processor reports the performance information generated, based on the time elapsed and the information about at least one of the load exercise session and the rest session.

7. A performance information notification method comprising:
    acquiring information about at least one exercise cycle by a sensor, the at least one exercise cycle including a load exercise session and rest session; and
    reporting performance information about a time during which the load exercise session is carried out in proportional relation to a time during which the rest session is carried out, based on the acquired information.

8. The performance information notification method according to claim 7, wherein
    the performance information includes at least one of a cumulative value of the time during which the load exercise session is carried out and a cumulative value of the time during which the rest session is carried out.

9. The performance information notification method according to claim 7, wherein
    the performance information includes at least one of a proportion of a cumulative value of the time during which the load exercise session is carried out to a total time of the exercise cycle, and a proportion of a cumulative value of the time during which the rest session is carried out to the total time of the exercise cycle.

10. The performance information notification method according to claim 9, wherein
    the performance information includes at least one of a time during which the load exercise session is carried out in the one exercise cycle and a time during which the rest session is carried out in the one exercise cycle.

11. The performance information notification method according to claim 7, wherein the acquiring includes acquiring information about a movement of a person detected by the sensor.

12. The performance information notification method according to claim 7, further comprising:
    measuring a time elapsed,
    wherein the reporting includes reporting the performance information generated, based on the time elapsed and the information about at least one of the load exercise session and the rest session.

13. A performance information notification device which displays, on a display screen:
- a proportion of a load exercise session which is a proportion of a cumulative value of a time during which the load exercise session is carried out to a time during which an interval exercise is carried out, the interval exercise being detected by a sensor and including the load exercise session and a rest session; and
- a proportion of the rest session which is a proportion of a cumulative value of a time during which the rest session is carried out to the time during which the interval exercise is carried out.

14. The performance information notification device according to claim 13, wherein
the proportion of the load exercise session and the proportion of the rest session are expressed by a graph.

15. A performance information notification device which displays, on a display screen:
- a proportion of a load exercise session which is a proportion of a time during which the load exercise session is carried out to a time during which one exercise cycle detected by a sensor and made up of one load exercise session and one rest session is carried out, and
- a proportion of the rest session which is a proportion of a time during which the rest session is carried out to the time during which the one exercise cycle is carried out.

16. The performance information notification device according to claim 15, wherein
the proportion of the load exercise session and the proportion of the rest session are expressed by a graph.

17. The performance information notification device according to claim 15, wherein
at least one of the time during which the load exercise session is carried out and the time during which the rest session is carried out is displayed on the display screen.

* * * * *